United States Patent [19]

Schade et al.

[11] Patent Number: 5,010,094
[45] Date of Patent: Apr. 23, 1991

[54] IMIDAZOLYL COMPOUNDS AND THEIR USE AS FUNGICIDES

[75] Inventors: Gerold Schade, Cologne; Albrecht Marhold, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 466,805

[22] Filed: Jan. 18, 1990

[30] Foreign Application Priority Data

Jan. 21, 1989 [DE] Fed. Rep. of Germany ....... 3901723

[51] Int. Cl.$^5$ .................... C07D 233/60; A01N 43/50
[52] U.S. Cl. ...................................... 514/399; 548/335
[58] Field of Search .......................... 548/335; 514/399

[56] References Cited

U.S. PATENT DOCUMENTS 4,780,471 10/1988 Maeda et al. ...................... 514/383

FOREIGN PATENT DOCUMENTS 0162359 11/1985 European Pat. Off. .
0297352 1/1989 European Pat. Off. .

*Primary Examiner*—David B. Springer
*Attorney, Agent, or Firm*—Sprung Horn Kramer & Woods

[57] ABSTRACT

Microbicidal, especially fungicidal, azolyl derivatives of the formula

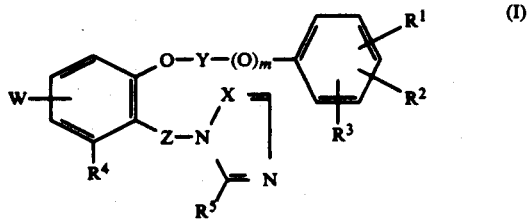

in which
$R^1$ represents halogenoalkyl or halogenoalkylthio,
$R^2$ represents hydrogen, halogen, cyano, optionally substituted alkyl, optionally substituted alkenyl, alkoxy, alkylthio, aryl or aryloxy,
$R^3$ represents hydrogen, halogen, cyano, optionally substituted alkyl, optionally substituted alkenyl, alkoxy, alkylthio, aryl or aryloxy,
$R^4$ represents hydrogen,
$R^5$ represents hydrogen or alkyl,
W represents hydrogen or halogen,
X represents nitrogen or a CH group,
Y represents alkylene,
m represents the number 0 or 1 and
Z represents the grouping

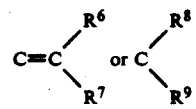

wherein
$R^6$ represents hydrogen, alkyl or optionally substituted phenyl, or
$R^6$, together with $R^4$, represents the grouping

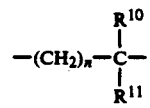

$R^7$ represents hydrogen or alkyl,
$R^8$ represents hydrogen or alkyl,
$R^9$ represents hydrogen or alkyl,
$R^{10}$ represents hydrogen or alkyl,
$R^{11}$ represents hydrogen or alkyl and
n represents the numbers 0, 1 or 2, and addition products thereof with acids and metal salts.

10 Claims, No Drawings

IMIDAZOLYL COMPOUNDS AND THEIR USE AS FUNGICIDES

The present invention relates to azolyl derivatives, a process for their preparation and their use as microbicides.

It is already known that numerous benzylimidazole derivatives can be used for combating fungi and bacteria (compare DE-OS (German Published Specification) 3,021,467, DE-OS (German Published Specification) 3,500,503 and EP-OS (European Published Specification) 0,162,359). Thus, for example, 1-(1-[2-thien-2-yl-methoxy)-phenyl]-vinyl)-imidazole and 1-(1-[2-(thien2-yl-methoxy)-phenyl]-2,2-dimethyl-vinyl)-imidazole can be used as fungicides against phytopathogenic fungi. If low amounts are applied, however, the activity of these substances in some cases leaves something to be desired.

New azolyl derivatives of the formula

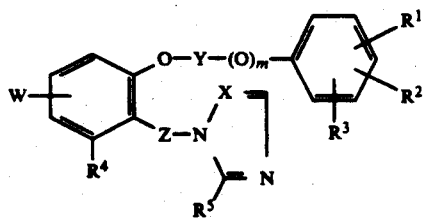

in which
R¹ represents halogenoalkyl or halogenoalkylthio,
R² represents hydrogen, halogen, cyano, optionally substituted alkyl, optionally substituted alkenyl, alkoxy, alkylthio, aryl or aryloxy,
R³ represents hydrogen, halogen, cyano, optionally substituted alkyl, optionally substituted alkenyl, alkoxy, alkylthio, aryl or aryloxy,
R⁴ represents hydrogen,
R⁵ represents hydrogen or alkyl,
W represents hydrogen or halogen,
X represents nitrogen or a CH group,
Y represents alkylene,
m represents the number 0 or 1 and
Z represents the grouping

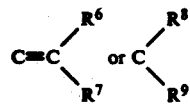

wherein
R⁶ represents hydrogen, alkyl or optionally substituted phenyl, or
R⁶, together with R⁴, represents the grouping

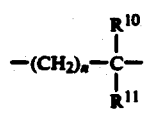

R⁷ represents hydrogen or alkyl,
R⁸ represents hydrogen or alkyl,
R⁹ represents hydrogen or alkyl,
R¹⁰ represents hydrogen or alkyl,
R¹¹ represents hydrogen or alkyl and n represents the number 0, 1 or 2,
and acid addition salts and metal salt complexes thereof have now been found.

It has furthermore been found that azolyl derivatives of the formula (I) and acid addition salts and metal salt complexes thereof are obtained by a process in which phenol derivatives of the formula

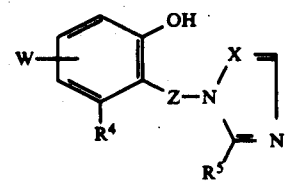

in which
R⁴, R⁵, W, X and Z have the abovementioned meanings,
are reacted with bases, if appropriate in the presence of a diluent, and the phenolates thereby formed, of the formula

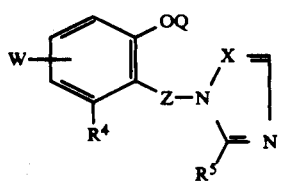

in which
R⁴, R⁵, W, X and Z have the abovementioned meanings and
Q represents a base radical,
are reacted with halogen compounds of the formula

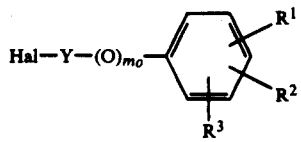

in which
R¹, R², R³, Y and m have the abovementioned meanings and
Hal represents chlorine, bromine or iodine,
in the presence of a diluent, and if appropriate in the presence of an acid-binding agent, and if appropriate an acid or a metal salt is then added onto the compounds of the formula (I) thus obtained.

It has moreover been found that the new azolyl derivatives of the formula (I) and acid addition salts and metal salt complexes thereof have very good microbicidal properties and can be employed in plant protection.

Surprisingly, in combating phytopathogenic fungi the substances according to the invention exhibit a significantly better activity than 1-(1-[2-(thien-2-yl-methoxy)-phenyl]-vinyl)-imidazole and 1-(1-[2-thien-2-yl-methoxy)-phenyl]-2,2-dimethyl-vinyl)-imidazole, which are structurally similar, already known compounds of the same type of action.

Formula (I) provides a general definition of the azolyl derivatives according to the invention. In this formula, preferably, R¹ represents halogenoalkyl having 1 to 4 carbon atoms and 1 to 5 identical or different halogen atoms, or represents halogenoalkylthio having 1 to 4 carbon atoms and 1 to 5 identical or different halogen atoms, R² represents hydrogen, fluorine, chlorine, bromine, cyano, optionally halogen-substituted alkyl having 1 to 6 carbon atoms, optionally halogen-substituted alkenyl having 2 to 6 carbon atoms, alkoxy having 1 to 4 carbon atoms, alkylthio having 1 to 4 carbon atoms, aryl having 6 to 10 carbon atoms or aryloxy having 6 to 10 carbon atoms, R³ represents hydrogen, fluorine, chlorine, bromine, cyano, optionally halogen-substituted alkyl having 1 to 6 carbon atoms, optionally halogen-substituted alkenyl having 2 to 6 carbon atoms, alkoxy having 1 to 4 carbon atoms, alkylthio having 1 to 4 carbon atoms, aryl having 6 to 10 carbon atoms or aryloxy having 6 to 10 carbon atoms, R⁴ represents hydrogen, R⁵ represents hydrogen or alkyl having 1 to 4 carbon atoms, W represents hydrogen, fluorine, chlorine or bromine, X represents nitrogen or a CH group, Y represents a straight-chain or branched alkylene chain having 1 to 6 carbon atoms, m represents the number 0 or 1 and represents the grouping

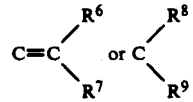

wherein

R⁶ represents hydrogen or alkyl having 1 to 4 carbon atoms, or represents phenyl which is optionally substituted by one to three identical or different substituents from the group comprising alkyl having 1 to 4 carbon atoms, halogen and/or halogenoalkyl having 1 or 2 carbon atoms and 1 to 5 halogen atoms, or R⁶, together with R⁴, represent the grouping

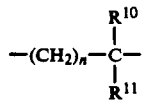

R⁷ represents hydrogen or alkyl having 1 to 4 carbon atoms,

R⁸ represents hydrogen or alkyl having 1 to 4 carbon atoms,

R⁹ represents hydrogen or alkyl having 1 to 4 carbon atoms,

R¹⁰ represents hydrogen or alkyl having 1 to 4 carbon atoms,

R¹¹ represents hydrogen or alkyl having 1 to 4 carbon atoms and n represents the number 0, 1 or 2.

Particularly preferred compounds of the formula (I) are those in which

R¹ represents halogenoalkyl having 1 or 2 carbon atoms and 1 to 5 identical or different halogen atoms, such as fluorine, chlorine and/or bromine, or represents halogenoalkylthio having 1 or 2 carbon atoms and 1 to 5 identical or different halogen atoms, such as fluorine, chlorine and/or bromine, R² represents hydrogen, fluorine, chlorine, bromine, cyano, alkyl having 1 to 4 carbon atoms which is optionally substituted by 1 to 3 fluorine, chlorine and/or bromine atoms, alkenyl having 2 to 4 carbon atoms which is optionally substituted by 1 to 3 fluorine, chlorine and/or bromine atoms, alkoxy having 1 or 2 carbon atoms, alkylthio having 1 or 2 carbon atoms, phenyl or phenoxy, R³ represents hydrogen, fluorine, chlorine, bromine, cyano, alkyl having 1 to 4 carbon atoms which is optionally substituted by 1 to 3 fluorine, chlorine and/or bromine atoms, alkenyl having 2 to 4 carbon atoms which is optionally substituted by 1 to 3 fluorine, chlorine and/or bromine atoms, alkoxy having 1 or 2 carbon atoms, alkylthio having 1 or 2 carbon atoms, phenyl or phenoxy, R⁴ represents hydrogen, R⁵ represents hydrogen, methyl or ethyl, W represents hydrogen or chlorine, X represents nitrogen or a CH group, Y represents a straight-chain or branched alkylene chain having 1 to 4 carbon atoms, m represents the number 0 or 1 and Z represents the grouping

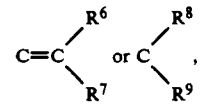

wherein

R⁶ represents hydrogen, methyl, ethyl, n-propyl, isopropyl or n-butyl, or represents phenyl which is optionally substituted by one to three identical or different substituents from the group comprising methyl, ethyl, fluorine, chlorine and/or trifluoromethyl, or R⁶, together with R⁴, represents the grouping

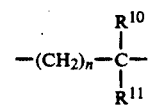

R⁷ represents hydrogen, methyl, ethyl, n-propyl, isopropyl or n-butyl,

R⁸ represents hydrogen, methyl, ethyl, n-propyl, isopropyl or n-butyl,

R⁹ represents hydrogen, methyl, ethyl, n-propyl, isopropyl or n-butyl,

R¹⁰ represents hydrogen or methyl,

R¹¹ represents hydrogen or methyl and n represents the number 0 or 1.

An especially preferred group of compounds comprises those substances of the formula (I) in which m represents the number 0, R¹ represents trifluoromethyl, dichlorofluoromethyl, difluorochloromethyl, difluorobromomethyl, trichloromethyl, fluoromethyl, difluoromethyl, trifluoroethyl, tetrafluoroethyl, trifluorochloroethyl pentafluoroethyl, trifluoromethylthio, difluoromethylthio, fluoromethylthio, difluorochloromethylthio, dichlorofluoromethylthio, difluoroethylthio, difluorobromomethylthio, trichloromethylthio, trifluoroethylthio, tetrafluoroethylthio, pentafluoroethylthio, trifluorochloroethylthio, trifluorodichloroethylthio or pentachloroethylthio, $R^2$ represents hydrogen, fluorine, chlorine, bromine, cyano, methyl, ethyl, trifluoromethyl, vinyl, allyl, 2-chlorovinyl, methoxy, methylthio, phenyl or phenoxy, $R^3$ represents hydrogen, fluorine, chlorine, bromine, cyano, methyl, ethyl, trifluoromethyl, vinyl, allyl, 2-chlorovinyl, methoxy, methylthio, phenyl or phenoxy, $R^4$ represents hydrogen, $R^5$ represents hydrogen, methyl or ethyl, W represents hydrogen or chlorine, X represents nitrogen or a CH group, Y represents methylene, ethylene, propylene or a group of the formula

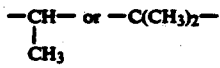

and
represents the grouping

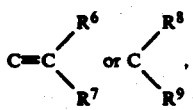

wherein $R^6$ represents hydrogen, methyl, ethyl, n-propyl, isopropyl or n-butyl, or represents phenyl which is optionally substituted by one to three identical or different substituents form the group comprising methyl, ethyl, fluorine, chlorine and/or trifluoromethyl, or $R^6$, together with $R^4$, represents the grouping

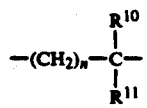

$R^7$ represents hydrogen, methyl, ethyl, n-propyl, isopropyl or n-butyl, $R^8$ represents hydrogen, methyl, ethyl, n-propyl, isopropyl or n-butyl, $R^9$ represents hydrogen, methyl, ethyl, n-propyl, isopropyl or n-butyl, $R^{10}$ represents hydrogen or methyl, $R^{11}$ represents hydrogen or methyl and n represents the numbers 0 or 1.

A further group of especially preferred compounds comprises those substances of the formula (I) in which m represents the number 1, $R^1$ represents trifluoromethyl, dichlorofluoromethyl, difluorochloromethyl, difluorobromomethyl, trichloromethyl, fluoromethyl, difluoromethyl, trifluoroethyl, tetrafluoroethyl, trifluorochloroethyl, pentafluoroethyl, trifluoromethylthio, difluoromethylthio, fluoromethylthio, difluorochloromethylthio, dichlorofluoromethylthio, difluoroethylthio, difluorobromomethylthio, trichloromethylthio, trifluoroethylthio, tetrafluoroethylthio, pentafluoroethylthio, trifluorochloroethylthio, trifluorodichloroethylthio or pentachloroethylthio, $R^2$ represents hydrogen, fluorine, chlorine, bromine, cyano, methyl, ethyl, trifluoromethyl, vinyl, allyl, 2-chlorovinyl, methoxy, methylthio, phenyl or phenoxy, $R^3$ represents hydrogen, fluorine, chlorine, bromine, cyano, methyl, ethyl, trifluoromethyl, vinyl, allyl, 2-chlorovinyl, methoxy, methylthio, phenyl or phenoxy, $R^4$ represents hydrogen, $R^5$ represents hydrogen, methyl or ethyl, W represents hydrogen or chlorine, X represents nitrogen or a CH group, Y represents methylene, ethylene, propylene or a group of the formula

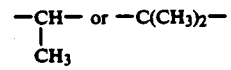

and
represents the grouping

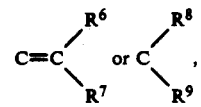

wherein $R^6$ represents hydrogen, methyl, ethyl, n-propyl, isopropyl or n-butyl, or represents phenyl which is optionally substituted by one to three identical or different substituents from the group comprising methyl, ethyl, fluorine, chlorine and/or trifluoromethyl, or $R^6$, together with $R^4$, represents the grouping

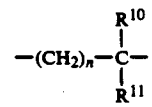

$R^7$ represents hydrogen, methyl, ethyl, n-propyl, isopropyl or n-butyl, $R^8$ represents hydrogen, methyl, ethyl, n-propyl, isopropyl or n-butyl, $R^9$ represents hydrogen, methyl, ethyl, n-propyl, isopropyl or n-butyl, $R^{10}$ represents hydrogen or methyl, $R^{11}$ represents hydrogen or methyl and n represents the number 0 or 1.

Addition products of acids and those azolyl derivatives of the formula (I) in which $R^1$, $R^2$, $R^3$, $R^4$, $R^5$, W, X, Y, Z and m have those meanings which have already been mentioned as preferred for these radicals and the index m are also preferred compounds according to the invention.

The acids which can be added on include, preferably, hydrogen halide acids, such as, for example, hydrochloric acid and hydrobromic acid, in particular hydrochloric acid, and furthermore phosphoric acid, nitric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

Addition products of salts of metals of main group II to IV and of sub-group I and II and IV to VIII of the periodic table of the elements and those azolyl derivatives of the formula (I) in which $R^1$, $R^2$, $R^3$, $R^4$, $R^5$, W, X, Y, Z and m have those meanings which have already been mentioned as preferred for these radicals and the index m are moreover preferred compounds according to the invention.

Salts of copper, zinc, manganese, magnesium, tin, iron and nickel are particularly preferred here. Possible anions of these salts are those which are derived from those acids which lead to physiologically tolerated addition products. Particularly preferred acids of this type are, in this connection, the hydrogen halide acids, such as, for example, hydrochloric acid and hydrobromic acid, and furthermore phosphoric acid, nitric acid and sulphuric acid.

The substances according to the invention can be in the form of cis- and trans-isomers if Z represents the grouping

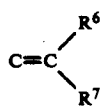

and $R^6$ and $R^7$ are different.

The invention relates both to the pure cis- and trans-isomers and to mixtures thereof.

If 1-[1-(2-hydroxyphenyl)-vinyl]-imidazole is used as the starting substance, sodium hydroxide is used as the base and 2-chloro-4-trifluoromethylthiobenzyl chloride is used as the reaction component, the course of the process according to the invention can be illustrated by the following equation.

principle (compare J. Med. Chem. 27. 1142 (1984) and DE-OS (German Published Specification) 3,021,467).

Possible bases in carrying out the process according to the invention are all the strong bases customary for such reactions. Bases which can preferably be used are alkali metal hydroxides, alkali metal amides, alkali metal alcoholates, alkali metal hydrides, quaternary ammonium hydroxides or phosphonium hydroxides. Sodium methylate, potassium tert.-butylate, sodium amide, sodium hydride and tetramethylammoniumhydroxide are particularly preferred. Q in formula (II-a) accordingly preferably represents an alkali metal cation, such as a sodium or potassium cation, or represents a quaternary ammonium or phosphonium cation.

Possible diluents in carrying out the first stage of the process according to the invention are all the organic solvents customary for such reactions. Solvents which can preferably be used are alcohols, such as methanol, ethanol, n-propanol, isopropanol, n-butanol and tert.-butanol.

The reaction temperatures can be varied within a substantial range in carrying out the first stage of the process according to the invention. In general, the reaction is carried out at temperatures between 0° C. and 100° C., preferably between 10° C. and 60° C.

In carrying out the first stage of the process according to the invention, the reaction is in general effected under normal pressure. However, it is also possible to carry out the reaction under increased or reduced pressure.

In carrying out the first stage of the process according to the invention, a procedure is in general followed

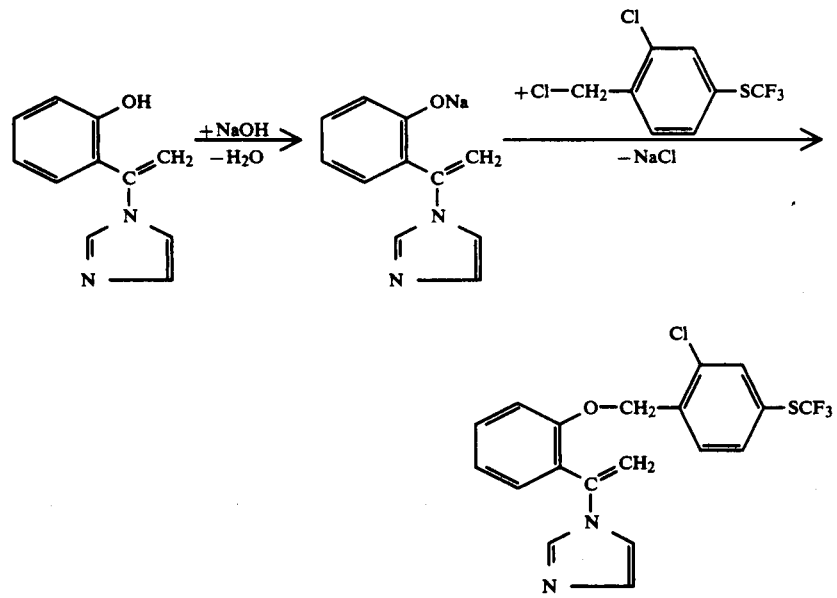

Formula (II) provides a general definition of the phenol derivatives required as starting substances in carrying out the process according to the invention. In this formula, $R^4$, $R^5$, W, X and Z preferably have those meanings which have already been mentioned as preferred for these radicals in connection with the description of the substances of the formula (I) according to the invention.

The phenol derivatives of the formula (II) are known or can be prepared by processes which are known in in which 1 mol of base is employed per mol of phenol derivative. However, it is also possible to employ one or the other of the components in an excess. Working-up is carried out by customary methods. In general, a procedure is followed in which the reaction mixture is concentrated by stripping off the diluent and the phenolate which thereby remains is used either directly or after prior purification for the subsequent synthesis.

Formula (III) provides a general definition of the halogen compounds used as reaction components in carrying out the second stage of the process according to the invention. In this formula, $R^1$, $R^2$, $R^3$, Y and m preferably have those meanings which have already been mentioned as preferred for these radicals and the index m in connection with the description of the substances of the formula (I) according to the invention. Hal represents chlorine, bromine or iodine.

The halogen compounds of the formula (III) are known (compare Synthesis 1983, 762 to 763).

The halogen compound of the formula

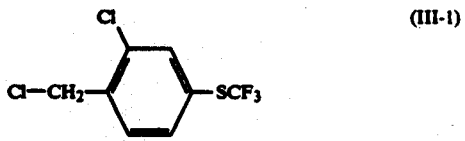
(III-1)

has not yet hitherto been disclosed. It can be prepared by reacting 2-chloro-4-trifluoromethylthio-toluene of the formula

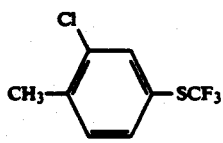

with chlorine.

The preparation of the 2-chloro-4-trifluoromethylthiobenzyl chloride of the formula (III-1) is in general carried out under reduced pressure, preferably under a pressure between 20 and 120 mbar.

The temperatures can be varied within a certain range in the preparation of the 2-chloro-4-trifluoromethylthiobenzyl chloride by the above process. The reaction is in general carried out at temperatures between 120° C. and 200° C., preferably between 140° C. and 180° C.

In carrying out the process for the preparation of the 2-chloro-4-trifluoromethylthiobenzyl chloride of the formula (III-1), a procedure is in general followed in which an excess of chlorine is added to 2-chloro-4-trifluoromethylthio-toluene and the components are allowed to react at the particular desired temperature under the particular desired pressure. Working-up is carried out by customary methods. In general, a procedure is followed in which the reaction mixture is distilled.

Possible diluents in carrying out the second stage of the process according to the invention are all the organic solvents customary for such reactions. Solvents which can preferably be used are alcohols, such as methanol, ethanol and butanol, and moreover ethers, such as diethyl ether, dioxane or tetrahydrofuran, and furthermore halogenated aliphatic hydrocarbons, such as methylene chloride, chloroform or carbon tetrachloride, and in addition nitriles, such as acetonitrile or propionitrile, and moreover amides, such as dimethylformamide, as well as strongly polar solvents, such as dimethylsulphoxide or hexamethylphosphoric acid triamide.

Possible acid-binding agents in carrying out the second stage of the process according to the invention are all the customary acid acceptors. Acid acceptors which can preferably be used are alkali metal carbonates and bicarbonates, such as sodium carbonate, potassium carbonate or sodium bicarbonate, and furthermore alkali metal hydroxides and alcoholates, such as sodium hydroxide, potassium hydroxide, sodium methylate or potassium tert.-butylate, and in addition tertiary aliphatic or aromatic amines, such as triethylamine, N,N-dimethylcyclohexylamine, N,N-dimethylbenzylamine and pyridine, and in addition cyclic amines, such as 1,5-diazabicyclo[4.3.0]non-5-ene (DBN), 1,8-diazabicyclo[5.4.0]undec-7ene (DBU) and 1,4-diazabicyclo[2.2.2]octane (DABCO).

The reaction temperatures can be varied within a substantial range in carrying out the second stage of the process according to the invention. The reaction is in general carried out at temperatures between 0° C. and 120° C., preferably between 10° C. and 100° C.

In carrying out the second stage of the process according to the invention, the reaction is in general performed under normal pressure. However, it is also possible to carry out the reaction under increased or reduced pressure.

In carrying out the second stage of the process according to the invention, in general 1 to 1.3 mols of halogen compound of the formula (III) are employed per mol of phenolate of the formula (II-a). Working-up is carried out by customary methods. A procedure is in general followed in which the reaction mixture is concentrated by stripping off the diluent and the residue which remains is purified by recrystallization or by a chromatographic route.

The compounds of the formula (I) obtainable by the process according to the invention can be converted into acid addition salts or metal salt complexes.

Those acids which have already been mentioned as preferred acids in connection with the description of the acid addition salts according to the invention are suitable for the preparation of acid addition salts of the compounds of the formula (I).

The acid addition salts of the compounds of the formula (I) can be obtained in a simple manner by customary salt formation methods, for example by dissolving a compound of the general formula (I) in a suitable inert solvent and adding the acid, for example hydrochloric acid, and they can be isolated in a known manner, for example by filtration, and if appropriate purified by washing with an inert organic solvent.

Those salts of metals which have already been described above are preferably suitable for the preparation of metal salt complexes of the compounds of the general formula (I).

The metal salt complexes of compounds of the general formula (I) can be obtained in a simple manner by customary processes, thus, for example, by dissolving the metal salt in alcohol, for example ethanol, and adding the solution to compounds of the general formula (I). The metal salt complexes can be isolated in a known manner, for example by filtration, and if appropriate purified by recrystallization.

The active compounds according to the invention exhibit a potent microbicidal action and can be employed as fungicides in plant protection.

Fungicides in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Xanthomonas species, such as *Xanthomonas oryzae*;
Pseudomonas species, such as *Pseudomonas lachrymans*;

Erwinia species, such as *Erwinia amylovora;*
Pythium species, such as *Pythium ultimum;*
Phytophthora species, such as *Phytophthora infestans;*
Pseudoperonospora species, such as *Pseudoperonospora humuli* or *Pseudoperonospora cubense;*
Plasmopara species, such as *Plasmopara viticola;*
Peronospora species, such as *Peronospora pisi* or *P. brassicae;*
Erysiphe species, such as *Erysiphe graminis;*
Sphaerotheca species, such as *Sphaerotheca fuliginea;*
Podosphaera species, such as *Podosphaera leucotricha;*
Venturia species, such as *Venturia inaequalis;*
Pyrenophora species, such as *Pyrenophora teres* or *P. graminae* (conidia form: Drechslera, syn: Helminthosporium);
Cochliobolus species, such as *Cochliobolus sativus;* (conidia form: Drechslera, syn: Helminthosporium);
Uromyces species, such as *Uromyces appendiculatus;*
Puccinia species, such as *Puccinia recondita;*
Tilletia species, such as *Tilletia caries;*
Ustilago species, such as *Ustilago nuda* or *Ustilago avenae;*
Pellicularia species, such as *Pellicularia sasakii;*
Pyricularia species, such as *Pyricularia oryzae;*
Fusarium species, such as *Fusarium culmorum;*
Botrytis species, such as *Botrytis cinerea;*
Septoria species, such as *Septoria nodorum;*
Leptosphaeria species, such as, *Leptosphaeria nodorum;*
Cercospora species, such as *Cercospora canescens;*
Alternaria species, such as *Alternaria brassicae* and Pseudocercosporella species such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In plant protection, the substances according to the invention exhibit a particularly good action against *Leptosphaeria nodorum* and against *Pyricularia oryzea.* They also have potent bactericidal properties and proved to be very effective in the agar plate test.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquid gases under pressure, and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionogenic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipides, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

When the substances according to the invention are used as fungicides, the amount applied can be varied within a substantial range according to the method application. Thus, in the treatment of parts of plants, the active compound concentrations in the use forms are in general between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02%, are required at the place of action.

The preparation and use of the active compounds according to the invention is illustrated by the following examples.

Preparation examples

EXAMPLE 1

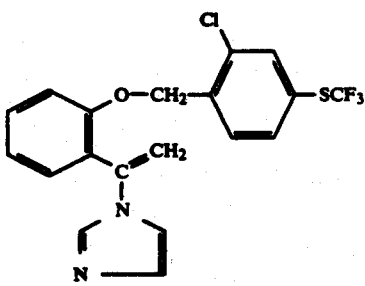

(I-1)

1.6 g (0.04 mol) of sodium hydroxide are added to a mixture of 7.44 g (0.04 mol) of 1-[1-(2-hydroxy-phenyl)-vinyl]-imidazole and 100 ml of methanol at room temperature, while stirring. When the addition has ended, the mixture is stirred at 50° C. for a further 30 minutes and then concentrated by stripping off the solvent under reduced pressure. The solid residue which remains is taken up in 100 ml of dimethylformamide. 11.5 g (0.044 mol) of 2-chloro-4-trifluoromethylthiobenzyl chloride are added dropwise to the solution formed. After the mixture has been heated at 100° C. for two hours, working-up is carried out by concentrating the mixture by stripping off the diluent. The residue obtained is chromatographed over silica gel using toluene-/ethyl acetate=1:1. 14.6 g (80.1% of theory) of 1-[1-(2-{2-chloro-4-trifluoromethyl-thiobenzyloxy}-phenyl)-vinyl]-imidazole are obtained in this manner in the form of a solid substance of melting point 67° C.

Preparation of the starting substance of the formula

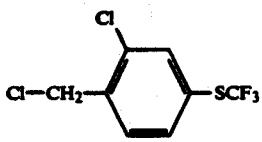

(III-1)

260 g (1.15 mol) of 3-chloro-4-(methyl)-trifluorothiomethylbenzene are heated under reflux in a round-bottomed flask provided with a Vigreux column, column head and cooled receiver (100% reflux). During this procedure, a slow stream of chlorine is introduced into the vapor phase via the column head. At 60% conversion, the reaction mixture is distilled over a 1 m rotating belt column. 151 g of 3-chloro-4-(chloromethyl)-trifluorothiomethyl-benzene is obtained in a yield of 88% (based on the conversion).

Boiling point=100°-102° C./12 mbar
$n_D^{20}$=1.5240

EXAMPLE 2

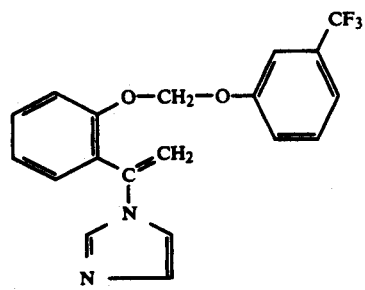

(I-2)

1.6 g (0.04 mol) of sodium hydroxide are added to a mixture of 7.4 g (0.04 mol) of 1-[1-(2-hydroxyphenyl)-vinyl]-imidazole and 100 ml of methanol at room temperature, while stirring. When the addition has ended, the mixture is stirred at 50° C. for a further 30 minutes and then concentrated by stripping off the solvent under reduced pressure. The solid residue which remains is taken up in 100 ml of dimethylformamide. 9.2 g (0.044 mol) of 1-chloromethyl-3-trifluoromethyl benzene are added dropwise to the solution formed. After the reaction mixture has been heated at 100° C. for one hour, it is worked up by stripping of the diluent under reduced pressure. The residue obtained is chromatographed over silica gel using toluene. 8.8 g of an oily product which, according to high performance liquid chromatography, consists of 1-[1-(2-{3-trifluoromethyl-phenoxymethoxy}-phenyl)-vinyl]-imidazole to the extent of 94.6% are obtained in this manner. The yield is accordingly calculated as 53.8% of theory.

$^1$H-NMR spectrum (DMSO, TMS); 250 MHz
δ: 4.9 and 5.5 ppm (s)

δ: 5.8 ppm (s) —O—CH$_2$—O—

EXAMPLE 3

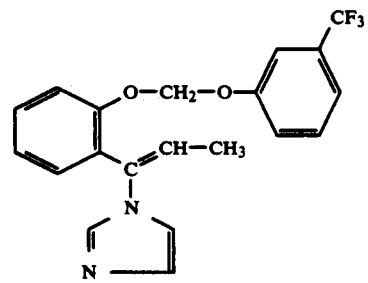

(I-3)

The compound of the formula (I-3) is also prepared by the methods described in Examples 1 and 2. The compound is obtained in the form of an oil. The structure shown is confirmed by the nuclear magnetic resonance spectrum. It is a cis/trans mixture.

$^1$H-NMR spectrum (DMSO, TMS); 250 MHz
δ: 1.35 (d) and 1.6 ppm (d) —CH$_3$
δ: 5.79 and 5.85 ppm (s) —O—CH$_2$—O—

The compounds shown below were employed as comparison substances in the use examples which follow.

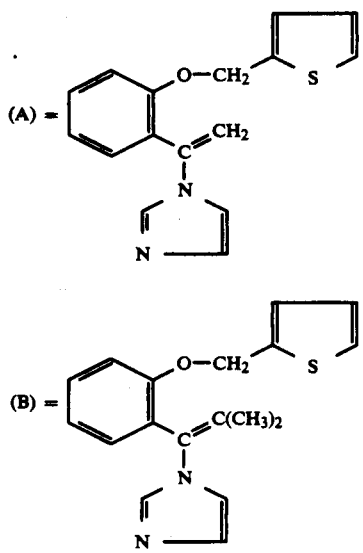

EXAMPLE A

Botrytis test (beans)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humid chamber at 20° C. 3 days after the inoculation, the size of the infected spots on the leaves is evaluated.

In this test, substances (I-1), (I-2) and (I-3) according to the invention exhibit a considerably better activity than comparison substances A and B.

EXAMPLE B

Pyrenophora teres test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew moist. After the spray coating has dried on, the plants are sprayed with a conidia suspension of *Pyrenophora teres*. The plants then remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, substances (I-1), (I-2) and (I-3) according to the invention exhibit a considerably better activity than comparison substances (A) and (B).

EXAMPLE C

Fusarium culmorum test (wheat)/seed treatment

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

2 batches of 100 grains of the wheat are sown 1 cm deep in standard soil and are cultivated in a greenhouse at a temperature of about 18° C. in seedboxes which are exposed to light for 15 hours daily.

About 3 weeks after sowing, the plants are evaluated for symptoms.

In this test, substances (I-2) and (I-3) according to the invention exhibit a considerably better activity than comparison substance (B).

It is understood that the specification and examples are illustrative but not limitative of the present invention and that other embodiments within the spirit and scope of the invention will suggest themselves to those skilled in the art.

We claim:

1. An axolyl derivative of the formula

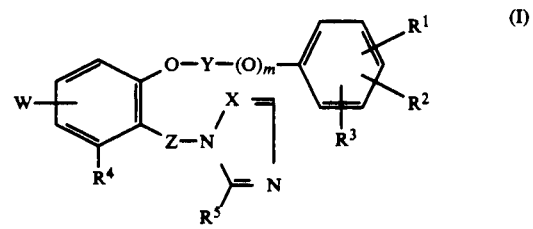

in which $R^1$ represents halogenoalkyl having 1 to 4 carbon atoms and 1 to 5 identical or different halogen atoms, or represents halogenoalkylthio having 1 to 4 carbon atoms and 1 to 5 identical or different halogen atoms, $R^2$ represents hydrogen, fluorine, chlorine, bromine, cyano, optionally halogen-substituted alkyl having 1 to 6 carbon atoms, optionally halogen-substituted alkenyl having 2 to 6 carbon atoms, alkoxy having 1 to 4 carbon atoms, alkylthio having 1 to 4 carbon atoms, aryl having 6 to 10 carbon atoms or aryloxy having 6 to 10 carbon atoms, $R^3$ represents hydrogen, fluorine, chlorine, bromine, cyano, optionally halogen-substituted alkyl having 1 to 6 carbon atoms, optionally halogen-substituted alkenyl having 2 to 6 carbon atoms, alkoxy having 1 to 4 carbon atoms, alkylthio having 1 to 4 carbon atoms, aryl having 6 to 10 carbon atoms or aryloxy having 6 to 10 carbon atoms, $R^4$ represents hydrogen, $R^5$ represents hydrogen or alkyl having 1 to 4 carbon atoms, W represents hydrogen, fluorine, chlorine, or bromine, X represents a CH group, Y represents a straight-chain or branched alkylene chain having 1 to 6 carbon atoms, m represents the number 0 or 1 and Z represents the grouping

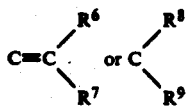

wherein $R^6$ represents hydrogen or alkyl having 1 to 4 carbon atoms, or represents phenyl which is optionally substituted by one to three identical or different substituents from the group comprising alkyl having 1 to 4 carbon atoms, halogen and/or halogenoalkyl having 1 or 2 carbon atoms and 1 to 5 halogen atoms, or $R^6$, together with $R^4$, represent the grouping

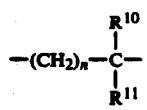

$R^7$ represents hydrogen or alkyl having 1 to 4 carbon atoms, $R^8$ represents hydrogen or alkyl having 1 to 4 carbon atoms, $R^9$ represents hydrogen or alkyl having 1 to 4 carbon atoms, $R^{10}$ represents hydrogen or alkyl having 1 to 4 carbon atoms, $R^{11}$ represents hydrogen or alkyl having 1 to 4 carbon atoms and n represents the number 0, 1, or 2.

2. An axolyl derivative to claim 1, in which $R^1$ represents halogenoalkyl having 1 or 2 carbon atoms and 1 to 5 identical or different halogen atoms or represents halogenoalkylthio having 1 or 2 carbon atoms and 1 to 5 identical or different halogen atoms, $R^2$ represents hydrogen, fluorine, chlorine, bromine, cyano, alkyl having 1 to 4 carbon atoms which is optionally substituted by 1 to 3 fluorine, chlorine and/or bromine atoms, alkenyl having 2 to 4 carbon atoms which is optionally substituted by 1 to 3 fluorine, chlorine and/or bromine atoms, alkoxy having 1 or 2 carbon atoms, alkylthio having 1 or 2 carbon atoms, phenyl or phenoxy, $R^3$ represents hydrogen, fluorine, chlorine, bromine, cyano, alkyl having 1 to 4 carbon atoms which is optionally substituted by 1 to 3 fluorine, chlorine and/or bromine atoms, alkenyl having 2 to 4 carbon atoms which is optionally substituted by 1 to 3 fluorine, chlorine and/or bromine atoms, alkoxy having 1 or 2 carbon atoms, alkylthio having 1 or 2 carbon atoms, phenyl or phenoxy, $R^4$ represents hydrogen, $R^5$ represents hydrogen, methyl or ethyl, W represents hydrogen or chlorine, X represents a CH group, Y represents a straight-chain or branched alkylene chain having 1 to 4 carbon atoms, m represents the number 0 or 1 and Z represents the grouping

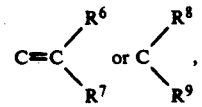

wherein $R^6$ represents hydrogen, methyl, ethyl, n-propyl, iso-propyl or n-butyl, or represents phenyl which is optionally substituted by one to three identical or different substituents from the group comprising methyl, ethyl, fluorine, chlorine and/or trifluoromethyl, or $R^6$, together with $R^4$, represents the grouping

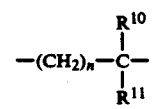

$R^7$ represents hydrogen, methyl, ethyl, n-propyl, isopropyl or n-butyl, $R^8$ represents hydrogen, methyl, ethyl, n-propyl, isopropyl or n-butyl, $R^9$ represents hydrogen, methyl, ethyl, n-propyl, isopropyl or n-butyl, $R^{10}$ represents hydrogen or methyl, $R^{11}$ represents hydrogen or methyl and n represents the number 0 or 1.

3. An axolyl derivative according to claim 1, in which m represents the number 0, $R^1$ represents trifluoromethyl, dichlorofluoromethyl, difluorochloromethyl, difluorobromomethyl, trichloromethyl, fluoromethyl, difluoromethyl, trifluoroethyl, tetrafluoroethyl, trifluorochloroethyl, pentafluoroethyl, trifluoromethylthio, difluoromethylthio, fluoromethylthio, difluorochloromethylthio, dichlorofluoromethylthio, difluoroethylthio, difluorobromomethylthio, trichloromethylthio, trifluoroethylthio, tetrafluoroethylthio, pentafluoroethylthio, trifluorochloroethylthio, trifluorodichloroethylthio or pentachloroethylthio, $R^2$ represents hydrogen, fluorine, chlorine, bromine, cyano, methyl, ethyl, trifluoromethyl, vinyl, allyl, 2-chlorovinyl, methoxy, methylthio, phenyl or phenoxy, $R^3$ represents hydrogen, fluorine, chlorine, bromine, cyano, methyl, ethyl, trifluoromethyl, vinyl, allyl, 2-chlorovinyl, methoxy, methylthio, phenyl or phenoxy, $R^4$ represents hydrogen, $R^5$ represents hydrogen, methyl or ethyl, W represents hydrogen or chlorine, X represents a CH group, Y represents methylene, ethylene, propylene or a group of the formula

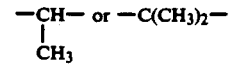

and

Z represents the grouping

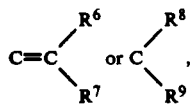

wherein
R⁶ represents hydrogen, methyl, ethyl, n-propyl, isopropyl or n-butyl, or represents phenyl which is optionally substituted by one to three identical or different substituents form the group comprising methyl, ethyl, fluorine, chlorine and/or trifluoromethyl, or
R⁶, together with R⁴, represents the grouping

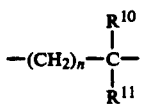

R⁷ represents hydrogen, methyl, ethyl, n-propyl, isopropyl or n-butyl,
R⁸ represents hydrogen, methyl, ethyl, n-propyl, isopropyl or n-butyl,
R⁹ represents hydrogen, methyl, ethyl, n-propyl, isopropyl or n-butyl,
R¹⁰ represents hydrogen or methyl,
R¹¹ represents hydrogen or methyl and
n represents the numbers 0 or 1.

4. An azolyl derivative according to claim 1, in which
m represents the number 1,
R¹ represents trifluoromethyl, dichlorofluoromethyl, difluorochloromethyl, difluorobromomethyl, trichloromethyl, fluoromethyl, difluoromethyl, trifluoroethyl, tetrafluoroethyl, trifluorochloroethyl, pentafluoroethyl, trifluoromethylthio, difluoromethylthio, fluoromethylthio, difluorochloromethylthio, dichlorofluoromethylthio, difluoroethylthio, difluorobromomethylthio, trichloromethylthio, trifluoroethylthio, tetrafluoroethylthio, pentafluoroethylthio, trifluorochloroethylthio, trifluorodichloroethylthio or pentachloroethylthio,
R² represents hydrogen, fluorine, chlorine, bromine, cyano, methyl, ethyl, trifluoromethyl, vinyl, allyl, 2-chlorovinyl, methoxy, methylthio, phenyl or phenoxy,
R³ represents hydrogen, fluorine, chlorine, bromine, cyano, methyl, ethyl, trifluoromethyl, vinyl, allyl, 2-chlorovinyl, methoxy, methylthio, phenyl or phenoxy,
R⁴ represents hydrogen,
R⁵ represents hydrogen, methyl or ethyl,
W represents hydrogen or chlorine,
X represents a CH group,
Y represents methylene, ethylene, propylene or a group of the formula

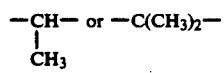

and
Z represents the grouping

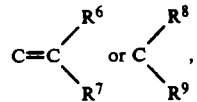

wherein
R⁶ represents hydrogen, methyl, ethyl, n-propyl, isopropyl or n-butyl, or represents phenyl which is optionally substituted by one to three identical or different substituents from the group comprising methyl, ethyl, fluorine, chlorine and/or trifluoromethyl, or
R⁶, together with R⁴, represents the grouping

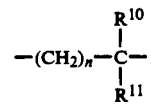

R⁷ represents hydrogen, methyl, ethyl, n-propyl, isopropyl or n-butyl,
R⁸ represents hydrogen, methyl, ethyl, n-propyl, isopropyl or n-butyl,
R⁹ represents hydrogen, methyl, ethyl, n-propyl, isopropyl or n-butyl,
R¹⁰ represents hydrogen or methyl,
R¹¹ represents hydrogen or methyl and
n represents the number 0 or 1.

5. An azolyl derivative according to claim 1, wherein such compound is 1-[1-(2-{2-chloro-4-trifluoromethyl}-phenyl)-vinyl]-imidazole of the formula

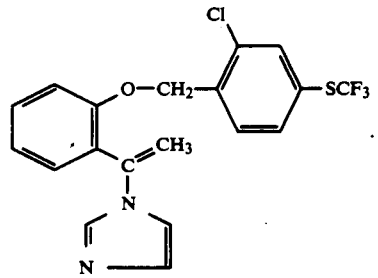

6. An azolyl derivative according to claim 1, wherein such compound is 1-[1-(2-{3-trifluoromethylphenoxymethoxy}-phenyl)-vinyl]-imidazole of the formula

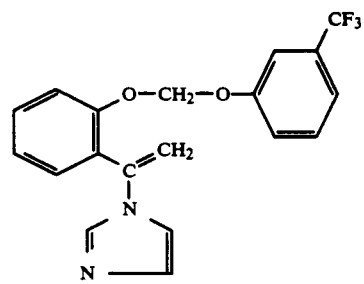

7. An azolyl derivative according to claim 1, wherein such compound is 1-[1-(2-{3-trifluoromethylphenoxymethoxy}-phenyl)-propenyl]-imidazole of the formula

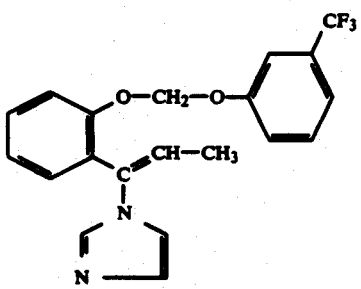

8. A fungicidal composition comprising a fungicidally effective amount of a compound or addition product thereof according to claim 1 and a diluent.

9. A method of combating fungi which comprises applying to such fungi or to a fungus habitat a fungicidally effective amount of a compound or addition product thereof according to claim 1.

10. The method according to claim 9, wherein such compound is

1-[1-(2-{2-chloro-4-trifluoromethylthiobenzyloxy}-phenyl)-vinyl]-imidazole,

1-[1-(2-{3-trifluoromethylphenoxymethoxy}-phenyl)-vinyl]-imidazole or

1-[1-(2-{3-trifluoromethylphenoxymethoxy}-phenyl)-propenyl]-imidazole.

* * * * *

UNITED STATES PATENT AND TRADEMARK OFFICE
CERTIFICATE OF CORRECTION

PATENT NO. : 5,010,094
DATED : April 23, 1991
INVENTOR(S) : Schade et al.

It is certified that error appears in the above-identified patent and that said Letters Patent is hereby corrected as shown below:

Col. 20 lines 37-47    Delete " 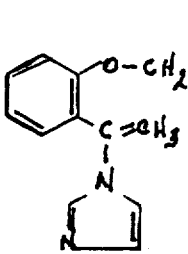 " and substitute

-- 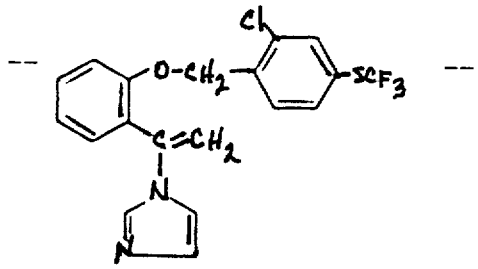 --

Signed and Sealed this

Twenty-seventh Day of April, 1993

Attest:

MICHAEL K. KIRK

Attesting Officer    Acting Commissioner of Patents and Trademarks